(12) United States Patent
Dollevoet et al.

(10) Patent No.: US 11,970,305 B2
(45) Date of Patent: Apr. 30, 2024

(54) METHOD FOR MANUFACTURING CUSTOM PRODUCTS

(71) Applicant: Kimberly-Clark Worldwide, Inc., Neenah, WI (US)

(72) Inventors: Tim G. Dollevoet, Kimberly, WI (US); Jeffrey R. Heller, Fond du Lac, WI (US); Steven T. Moore, Appleton, WI (US); Manan Gill, Grand Chute, WI (US); Jason A. Verboomen, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 711 days.

(21) Appl. No.: 17/054,723

(22) PCT Filed: May 30, 2019

(86) PCT No.: PCT/US2019/034665
§ 371 (c)(1),
(2) Date: Nov. 11, 2020

(87) PCT Pub. No.: WO2019/232219
PCT Pub. Date: Dec. 5, 2019

(65) Prior Publication Data
US 2021/0300613 A1    Sep. 30, 2021

Related U.S. Application Data

(60) Provisional application No. 62/678,459, filed on May 31, 2018.

(51) Int. Cl.
*B65B 61/02* (2006.01)
*A61F 13/15* (2006.01)
(Continued)

(52) U.S. Cl.
CPC ...... *B65B 61/025* (2013.01); *A61F 13/15747* (2013.01); *A61F 13/84* (2013.01);
(Continued)

(58) Field of Classification Search
CPC ......... B65B 61/025; B65B 5/06; B65B 57/10; B65B 2210/04; B65B 2220/14
(Continued)

(56) References Cited

U.S. PATENT DOCUMENTS

| 6,106,094 A | 8/2000 | Otani et al. |
|---|---|---|
| 6,347,856 B1 | 2/2002 | Arquilevich et al. |

(Continued)

FOREIGN PATENT DOCUMENTS

| CN | 102502325 A | 6/2012 |
|---|---|---|
| CN | 104981824 A | 10/2015 |

(Continued)

OTHER PUBLICATIONS

Co-pending U.S. Appl. No. 17/054,728, filed Nov. 11, 2020, by Dollevoet et al. for "Method For Manufacturing Custom Products."

*Primary Examiner* — Jacob A Smith
(74) *Attorney, Agent, or Firm* — KIMBERLY-CLARK WORLDWIDE, INC.

(57) ABSTRACT

Methods and apparatuses for manufacturing products having custom graphic designed are disclosed. A method may comprise printing a first order identifier graphic on a substrate material, the first order identifier graphic associated with a first order for a first set of products, printing a first set of one or more graphic designs on the material, the first set of one or more graphic designs associated with the first order, and combining the material with one or more product components to form a first set of products, each of the first set of products being associated with the first customer order and at least one of the products of the first set of products
(Continued)

comprising the first order identifier graphic. The method may further comprise packaging the first set of products in a first package wherein the first order identifier graphic is visible through the first package.

13 Claims, 6 Drawing Sheets

(51) Int. Cl.
*A61F 13/84* (2006.01)
*B65B 5/06* (2006.01)
*B65B 57/10* (2006.01)
(52) U.S. Cl.
CPC ............... *B65B 5/06* (2013.01); *B65B 57/10* (2013.01); *A61F 2013/8497* (2013.01); *B65B 2210/04* (2013.01); *B65B 2220/14* (2013.01)
(58) Field of Classification Search
USPC .......................................................... 53/411
See application file for complete search history.

(56) References Cited

U.S. PATENT DOCUMENTS

| | | |
|---|---|---|
| 6,871,110 B1 | 3/2005 | Yen et al. |
| 8,310,696 B2 | 11/2012 | Gustafson et al. |
| 8,503,015 B2 | 8/2013 | Gustafson et al. |
| 8,555,605 B2 | 10/2013 | Schmitz |
| 8,736,885 B2 | 5/2014 | Gustafson et al. |
| 8,807,684 B2 | 8/2014 | Allworth et al. |
| 8,958,104 B2 | 2/2015 | Comstock et al. |
| 9,058,584 B2 | 6/2015 | Fradet et al. |
| 9,111,310 B2 | 8/2015 | Comstock et al. |
| 9,665,847 B2 | 5/2017 | Fradet et al. |
| 9,776,810 B2 | 10/2017 | Collombet et al. |
| 9,792,514 B2 | 10/2017 | Ukishima |
| 9,868,311 B2 | 1/2018 | Dugge et al. |
| 9,937,706 B2 | 4/2018 | Yamazaki |
| 9,944,104 B2 | 4/2018 | Ukishima |
| 10,011,387 B1 | 7/2018 | Payauys |
| 2002/0152001 A1* | 10/2002 | Knipp .................. G06Q 10/087 700/95 |
| 2004/0143231 A1 | 7/2004 | Nair et al. |
| 2008/0110984 A1 | 5/2008 | Uchitani |
| 2009/0082747 A1 | 3/2009 | Carlen et al. |
| 2010/0232716 A1 | 9/2010 | Sanders |
| 2012/0279409 A1 | 11/2012 | Aylward et al. |
| 2013/0098795 A1 | 4/2013 | Biber |
| 2013/0262260 A1 | 10/2013 | Giloh et al. |
| 2014/0318996 A1* | 10/2014 | Schneider ............. B65D 79/00 206/281 |
| 2016/0350828 A1 | 12/2016 | Schmidt et al. |
| 2017/0120647 A1 | 5/2017 | Kyoso |
| 2017/0312136 A1* | 11/2017 | Koebel ................ B41M 5/0047 |
| 2018/0005290 A1 | 1/2018 | Warzala et al. |
| 2018/0032951 A1 | 2/2018 | Chanez et al. |
| 2018/0086049 A1 | 3/2018 | Ueshima |
| 2018/0139507 A1 | 5/2018 | Toksoz et al. |
| 2019/0197789 A1 | 6/2019 | Macauley et al. |
| 2022/0143999 A1 | 5/2022 | Miyato et al. |

FOREIGN PATENT DOCUMENTS

| | | | |
|---|---|---|---|
| CN | 105460280 A | 4/2016 | |
| CN | 106651851 A | 5/2017 | |
| CN | 107844516 A | 3/2018 | |
| CN | 108009613 A | 5/2018 | |
| DE | 4304748 A1 | 8/1994 | |
| EP | 3730413 A1 | 10/2020 | |
| JP | 2012139867 A | 7/2012 | |
| WO | 2014028204 A1 | 2/2014 | |
| WO | 14122479 A2 | 8/2014 | |
| WO | 17014696 A1 | 1/2017 | |
| WO | WO-2017014696 A1 * | 1/2017 | ............. A41D 13/11 |

* cited by examiner

METHOD FOR MANUFACTURING CUSTOM PRODUCTS

TECHNICAL FIELD

The present disclosure is directed to manufacturing custom products, and more particularly to manufacturing products with custom selected or designed graphics.

BACKGROUND OF THE DISCLOSURE

Custom manufactured products are increasing in consumer popularity. Some consumers may prefer purchasing products in which one or more features of the products are selected by the consumer. In particular, some consumers may desire an ability to select or design the graphic designs of the products they purchase.

Manufacturing such products with custom selected or designed graphic designs can present many manufacturing challenges. Current high-speed digital printing techniques allow for changing of the graphic design from one product to the next on a manufacturing line. However, such capabilities require increasingly complex tracking systems to track orders during manufacture, inspection systems to inspect individual products for not only product quality but also the desired graphic designs, and packaging systems to ensure the products with the selected graphic designs are matched with the consumer who placed the order. Accordingly, methods and apparatuses are continually desired which are able to successfully manufacture, inspect, and package products with custom designs matched to specific orders.

SUMMARY OF THE DISCLOSURE

The disclosure is directed to several methods and apparatuses for manufacturing products with custom selected or designed graphics.

In a first illustrative example, a method of manufacturing products having graphic designs may comprise printing a first order identifier graphic on a substrate material, the first order identifier graphic associated with a first order for a first set of products, printing a first set of one or more graphic designs on the first substrate material, the first set of one or more graphic designs associated with the first order, and combining the first substrate material with one or more product components to form the first set of products, each of the products of the first set of products being associated with the first customer order and at least one of the products of the first set of products comprising the first order identifier graphic. The method may further comprise packaging the first set of products in a first package wherein the first order identifier graphic is visible through the first package.

In a second illustrative embodiment, a method of manufacturing and packaging products having graphic designs with a manufacturing and packaging apparatus comprising a product stacker comprising slots may comprise combining, with the manufacturing and packaging apparatus, a first substrate material having a series of graphic designs printed thereon with one or more product components to form a series of products, the series of products comprising a first set of products associated with a first customer order and one product of the first set of products comprising a first order identifier graphic, the first order identifier graphic associated with the first customer order, scanning, with the manufacturing and packaging apparatus, the first order identifier graphic with a scanner and determining if the first order identifier graphic is a primary order identifier, and after determining that the first order identifier graphic is a primary order identifier, inserting a predetermined number of empty slots into the product stacker.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The aspects of the disclosure may be further understood in consideration of the following detailed description of various embodiments in connection with the accompanying drawings, in which.

Figure 1:
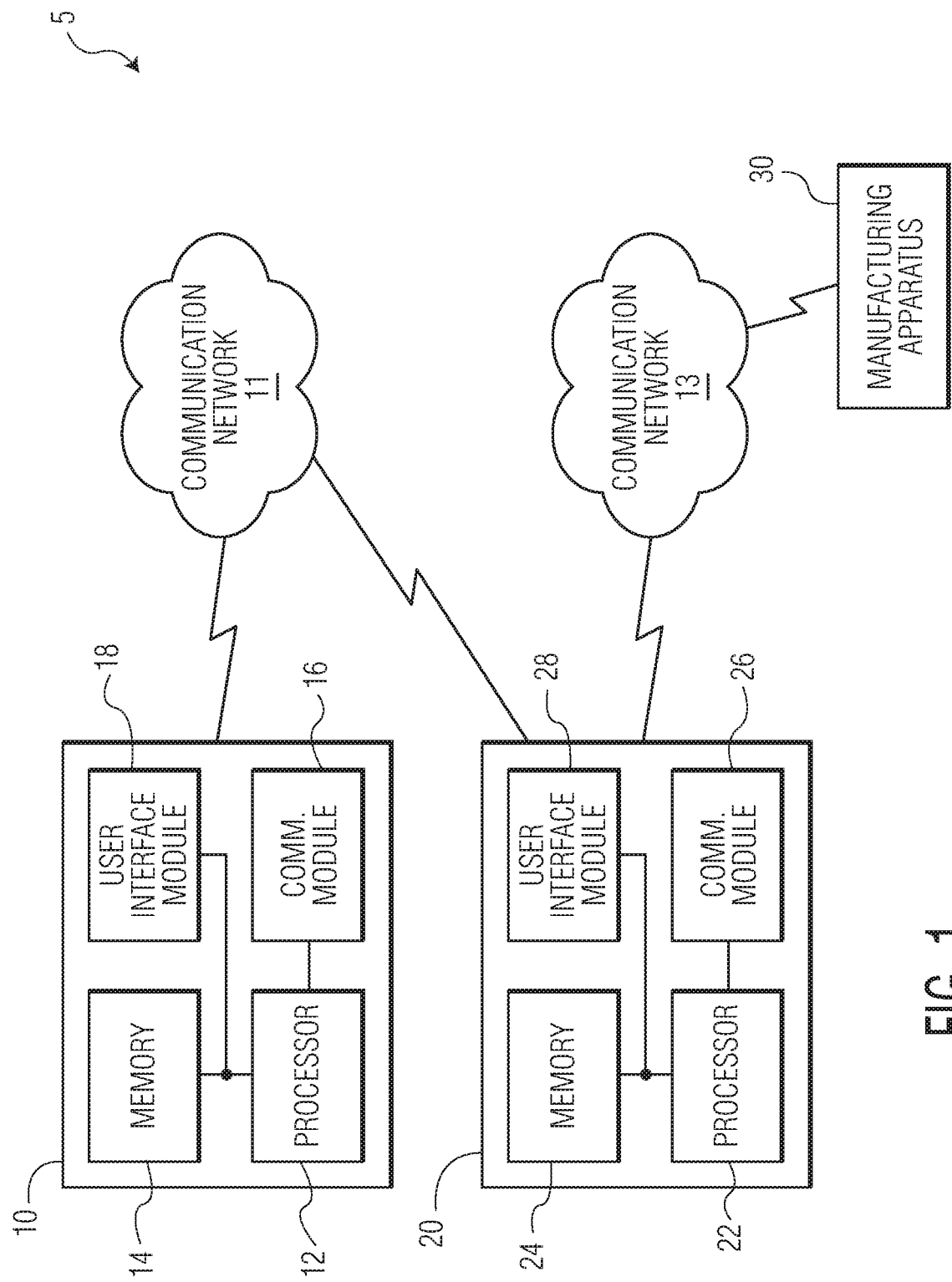
FIG. 1 is a schematic depiction of a system for manufacturing products with custom selected or designed graphics, according to aspects of the present disclosure.

Repeat use of reference characters in the present specification and drawings is intended to represent the same or analogous features or elements of the disclosure. Additionally, while the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION OF THE DISCLOSURE

The present disclosure is generally directed towards methods and apparatuses for manufacturing products with custom selected or designed graphics. In some embodiments, a test product may be added to a to-be-manufactured series of products comprising a customer order. The test product may comprise a print test graphic which is the only graphic inspected for quality of the series of products comprising the custom order. For example, a determination to cull the products of the customer order and re-manufacture the customer order may be based on a graphic inspection of only the print test graphic of the test product. The test product may further be placed in a primary packaging, such as a clear plastic bag, with the products of the customer order. Subsequently, the test product may be removed from the primary packaging and the remaining products of the customer order may be packaged in a secondary packaging. Alternatively, the test product with the products of the customer order may be placed in a secondary packaging, and the test product may be removed from the primary and secondary packaging before the rest of the products of a consumer order are packaged in a tertiary packaging.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "light transmittance" or "light transmission" refers herein to a measured property of a substrate, or substrates, as defined by the Light Transmittance Test further described herein.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat.

No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, training pant, youth pant, incontinent product, or other absorbent article about the wearer of one of these absorbent articles. A user and a wearer can be one and the same person.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 is a schematic drawing of system 5 comprising a system for manufacturing products having custom selected or designed graphic designs. Client device 10 may comprise a processor 12, a memory 14, a communication module 16, and a user interface module 18. The client device 10 may be connected through a communication network 11 to a server device 20, which may comprise a processor 22, a memory 24, a communication module 16, and a user interface module 28. The client device 10 may communicate with the server device 20 through the communication network 11.

A customer may initiate a request for purchasing one or more products through the client device 10, termed an order or customer order herein. For example, the customer may interact with the client device 10 through the user interface module 16. This interaction may cause the processor 12 to request information from the server device 20 through communication module 16. The server device 20 may receive the request through communication module 26, and the processor 22 may retrieve the requested information from the memory 24 and communicate the requested information to the client device 10 through the communication module 26.

The information communicated by the server device 20 may be an interactive product ordering website, which allows the customer, through interaction with the client device 10, to input one or more pieces of information, make one or more selections, and pay for one or more products, thereby generating a customer order. In some embodiments, the customer may input information such as a type of product the customer desires to order. In some particular embodiments according to the present disclosure, the type of product may be an absorbent article product. However, it should be understood that the specific type of products described herein are not meant to limit the disclosure, as the described manufacturing methods may be applicable to a broad range of products beyond just absorbent articles.

The information may further include an order quantity, a product size (for example, size 1-6 or small, medium, or large) or sub-type (for example, light, medium, heavy). In some embodiments, the information may further include a name, age, birthdate, gender, waist size, and/or weight. The information can also include an order date and time and/or address of the customer and/or and address of an intended recipient of the products of the order (e.g. a shipping address). Further, the information may include a selection of one or more graphic designs and/or input text information. In some embodiments, the customer may upload one or more custom graphic designs to the client device 10, such as through user interface module 18, to use as a selection(s) for the graphic designs of the one or more products of the order. Where multiple graphic designs are selected or uploaded, the information may further include a number of the products associated with each of the selected designs.

The input and/or uploaded information may be communicated to the server device 20 through communication network 11. The server device 20 may store the received information in the memory 24. The server device 20 may further perform one or more functions related to the received information, as will be described in more detail below. The server device 20 may communicate information to manufacturing apparatus 30 in order to initiate manufacture of the products according to the received customer order.

It should be understood that FIG. 1 depicts only one exemplary system which may implement the methods and processes described herein. In other embodiments, the system could contain one or more additional devices and the described inputting, processing, and/or storing steps may be split between the devices in any manner to achieve the described function of system 5. For example, the server device 20 may communicate the interactive website to the client device 10. However, the information input and/or uploaded to the client device 10 may be communicated to a third device (not shown) which is in communication with the manufacturing apparatus 30. Such a third device may be the device which performs the functions described below, including communicating with the manufacturing apparatus 30 to initiate manufacture of the products of the customer order. Accordingly, the methods and processes of the present disclosure should not be considered limited in implementation by the specific configuration of system 5 of FIG. 1. Other systems which are capable of implementing the methods and processes of the present disclosure are within the scope of this disclosure.

The processors 12, 22 may be any conventional processing device that can be configured to implement functionality and/or process instructions for execution within the devices 10, 20. The processors 12, 22 may be capable of processing instructions stored in memories 14, 24. For example, the processors 12, 22 may be what is conventionally known as a central processing unit (CPU), a microprocessor, or one of many types of microcontrollers.

The memories 14, 24 may be configured to store information within the devices 10, 20 during operation. The memories 14, 24 may, in some examples, be described as computer-readable storage media. In some examples, the memories 14, 24 are temporary memory, meaning that a primary purpose of the memories 14, 24 is not long-term storage. The memories 14, 24 may also be described as volatile memories, meaning that the memories 14, 24 do not maintain stored contents when the computer is turned off. Examples of volatile memories include random access memories (RAM), dynamic random-access memories (DRAM), static random-access memories (SRAM), and other forms of volatile memories known in the art. In some examples, the memories 14, 24 may be used to store program instructions for execution by the processors 12, 22. The memories 14, 24 may be used by software or applications running on the devices 10, 20 to temporarily store information during program execution. In some embodiments, the memories 14, 24 may comprise both volatile memory and non-volatile memory. Such non-volatile memory may also include one or more computer-readable storage media. Examples of non-volatile memory include magnetic hard discs, optical discs, floppy discs, flash memories, or forms of electrically programmable memories (EPROM) or electrically erasable and programmable (EEPROM) memories.

As briefly described above, the communication modules 16, 26 may allow the devices 10, 20 to communicate with other devices via one or more networks, such as communication networks 11 and/or 13. The communication modules 16, 26 may comprise components capable of communicating through wired and/or wireless networks. In some embodiments, the communication modules 16, 26 may include components for communicating over wire, Wi-Fi, and/or Bluetooth. Accordingly, the communication networks 11, 13 may represent wired, Wi-Fi, and/or Bluetooth networks. It should be understood, however, that these are just some example networks that the system 5 may use to communicate. The present disclosure contemplates the use of any type of network for communication between the various devices of the system implementing the methods and processes of the present disclosure.

Figure 2:
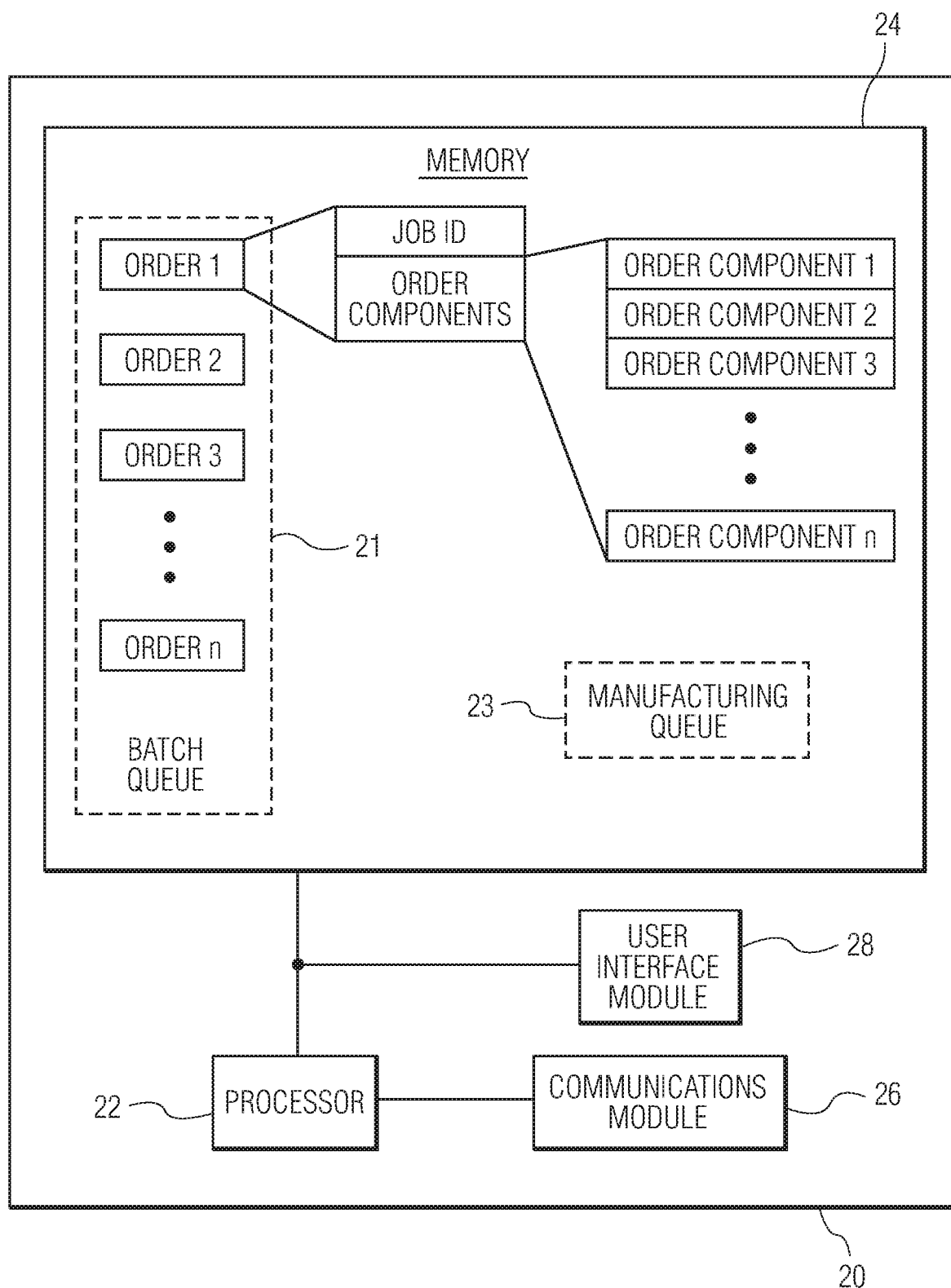
FIG. 2 is a schematic depiction of a server device, according to aspects of the present disclosure.

FIG. 2 is a schematic drawing of the server device 20 including information stored in the memory 24. The server device 20 may receive information included with a customer order from the client device 10. The server device 20 may store the received information in the memory 24 as shown by ORDER 1, ORDER 2, and ORDER 3 in FIG. 2, each representing a unique received customer order. Upon or after receiving a customer order (and associated information), the server device 20 may generate a unique JOB ID parameter and associate the JOB ID with a specific customer order, such as ORDER 1. The JOB ID parameter may be a numerical parameter, or any other parameter type, that can be used as a reference to a customer order, such as ORDER 1, ORDER 2, ORDER 3, or the like. The server device 20 may further generate one or more order component parameters from the information received with the customer order. These order components 1 through n may comprise individual entries in the memory 24 comprising the information that the user selected and/or input during the ordering process—e.g. article type, size and/or sub-type, article quantity, and/or the selected or uploaded graphic design for use on the product.

As can be seen in FIG. 2, the server device 20 may store the received customer orders in a batch queue 21. The batch queue 21 represents a holding space for the customer orders before the customer orders are batched into a manufacturing queue 23. In some embodiments, the server device 20 may be configured to form the manufacturing queue 23 from the customer orders within the batch queue 21 on a periodic basis. For example, the server device 20 may be configured to form a manufacturing queue 23 from the contents of the batch queue 21 once daily, every two days, every three days, weekly, or the like. Alternatively, the server device 20 may be configured to form a manufacturing queue 23 from the orders contained in the batch queue 21 when a threshold number of orders are in the batch queue 21.

The manufacturing queue 23 may generally comprise a sequential listing of JOB IDs, representing individual customer orders. The manner in which the server device 20 compiles the manufacturing queue 23 may differ in different embodiments. In some embodiments, the server device 20 may compile the manufacturing queue 23 such that the JOB IDs are ordered beginning with the JOB IDs associated with the earliest order date and time (which may be stored as an order component associated with the JOB IDs). Alternatively, the server device 20 may compile the manufacturing queue 23 such that the JOB IDs are ordered beginning with the JOB IDs associated with the most recent order date and time. In still other embodiments, the JOB IDs may be arranged such that JOB IDs with the same selected graphic design(s) are grouped together. In still further embodiments, the JOB IDs may be grouped by geographic region (e.g. country, state, county) of the recipient of the order (e.g. the shipping address).

In at least one embodiment, the server device 20 may compile the manufacturing queue 23 in order to produce one or more series of JOB IDs comprising a requisite quantity of products. For example, each JOB ID may have an associated order component detailing a quantity of products associated with that JOB ID. The system 900, described in more detail with respect to FIG. 6, may be configured to package a set quantity of products within a single package. The set quantity may be termed a bag quantity herein. To allow for customers to order a number of products less than the bag quantity for which the system 900 is configured, the server device 20 may form the manufacturing queue 23 to place JOB IDs associated with quantities of products, each individually less than a bag quantity, which add up to the bag quantity adjacent to each other in the manufacturing queue 23. As one illustrative example, where the bag quantity is thirty, the server device 20 may form the manufacturing queue 23 by placing JOB IDs associated with quantities of products having values of ten, eight, four, six and two, which when added together equal the bag quantity of thirty, adjacent to each other in the manufacturing queue 23.

After compiling the manufacturing queue 23, the server device 20 may communicate the manufacturing queue 23 to the manufacturing apparatus 30 and instruct the manufacturing apparatus 30 to manufacture products according to the information associated with each JOB ID. For instance, the manufacturing apparatus may manufacture the quantity of products associated with each JOB ID, the products having the graphic designs associated with the JOB ID. In some embodiments, the manufacturing apparatus 30 may comprise multiple sub-apparatuses, such as a printing apparatus and a product forming apparatus. In what will be termed an off-line manufacturing embodiment herein, the server device 20 may communicate the manufacturing queue 23 to a printing apparatus in order to print the graphic designs onto a substrate material according to the manufacturing queue 23.

Figure 3:
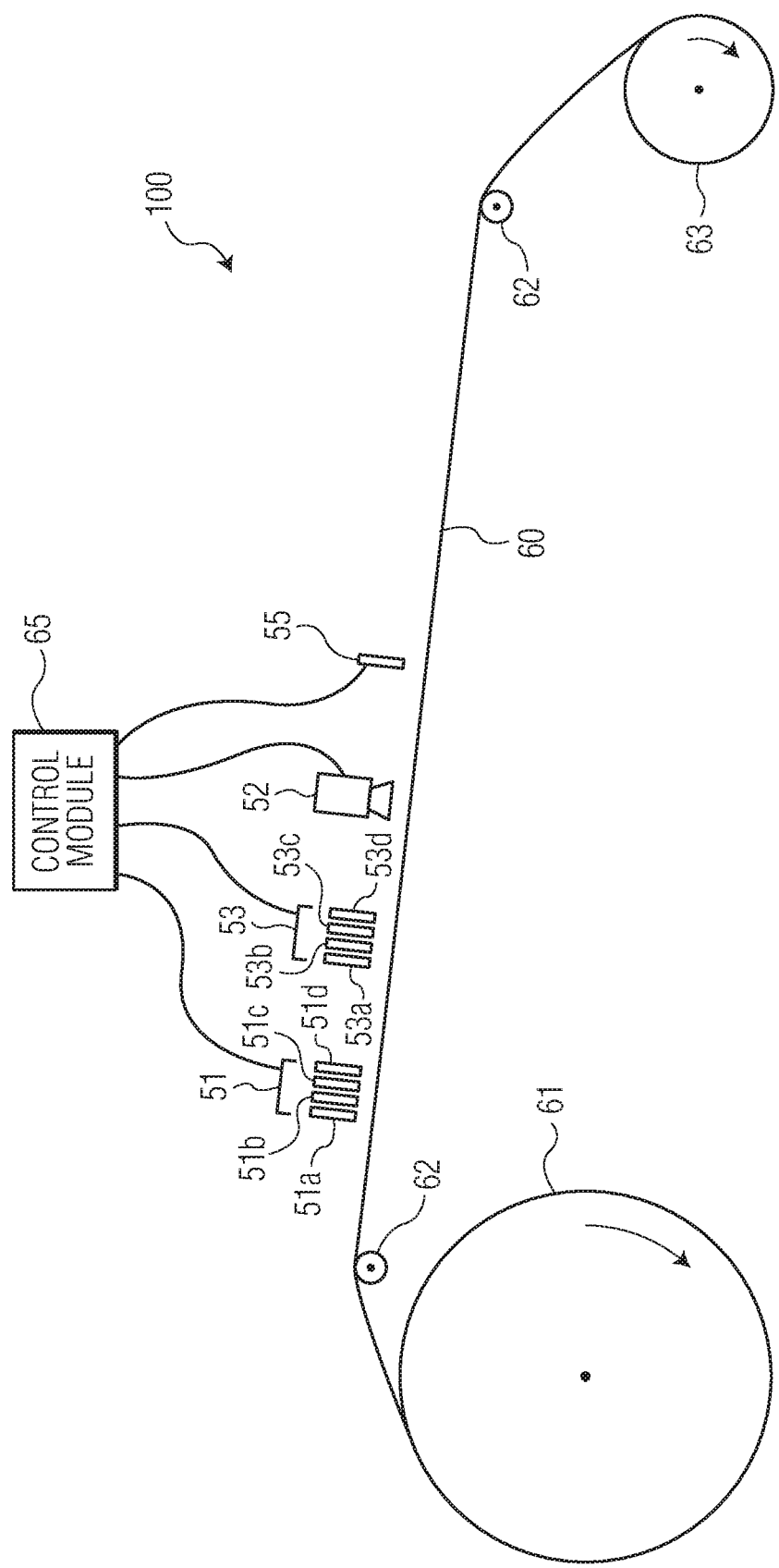
FIG. 3 is a schematic depiction of an exemplary printing system, according to aspects of the present disclosure.

FIG. 3 is a schematic depiction of an exemplary printing apparatus 100 which may be used to print the graphic designs associated with the customer orders, according to aspects of the present disclosure. The printing apparatus 100 may comprise roll 61 comprising an un-printed substrate material 60. The substrate material 60 may be unwound from roll 61 and pass over one or more guide rolls 62. The substrate material 60 may also pass under first print station 51 and second print station 53. Each of the first and second print stations 51, 53 may comprise four separate print bars 51a-d, 53a-d. The print bars 51a-d, 53a-d may span the substrate material 60 in the cross-machine direction (CD) for a distance covering a width of the substrate material 60 where the graphic design is to be located. Each of the print bars 51a-d, 53a-d may comprise multiple print heads disposed adjacent one another in the CD. In some embodiments, each of the print bars 51a-d, 53a-d may comprise two print heads, three print heads, four print heads, five print heads, or any other suitable number of print heads.

Each of the print bars 51a-d, 53a-d may be configured to print a single color. In some embodiments, separate ones of the print bars 51a-d may be configured to print black ink, cyan ink, magenta ink, and yellow ink. The print bars 53a-d may be configured in a similar way to the print bars 51a-d. In this manner, the print station 53 may be configured as a redundant print station to the print station 51 and may only operate when the print station 51 has a malfunction. In other embodiments, the print stations 51 and 53 may operate in coordination with each other to print the desired graphic designs onto the substrate material 60. In such embodiments, the substrate material 60 may be moved past the print stations 51, 53 at a line speed faster than the maximum firing speeds of the print heads of the print stations 51, 53 such that the print stations individually are unable to print the graphic designs at a print desired resolution (measured in dots-per-inch or DPI). In such embodiments, the two print stations 51, 53 may both print portions of the same graphic designs, there by achieving a higher print resolution than either of the print stations could achieve individually at the high line speed, according to well-known techniques in the art.

After passing under the first and second print stations 51, 53, the substrate material 60 may then continue on through the apparatus 100 and eventually be wound up into a new roll of printed-substrate material 63. This printed-substrate material 63 may then be transported to a product manufacturing apparatus to be combined with one or more different product components to form the products of the customer order. The substrate material 60 may pass through one or more other components of the printing apparatus 100, such as scanner 52 and print station 55, which will be described in more detail below.

Accordingly, once the printing apparatus 100 has received a manufacturing queue 23 from the server device 20 and an instruction to begin the printing process, the printing apparatus 100 may begin to print the graphic designs associated with the JOB IDs of the manufacturing queue 23. For the first JOB ID in the manufacturing queue 23, the printing apparatus 100 may be configured to print a number of the graphic designs equal to the order quantity associated with the first JOB ID plus an extra number of graphic designs. The extra number of graphic designs may be a value equal to between about 1% and about 30% of the order quantity, rounded up to the nearest whole number. In other embodiments, the extra number of graphic designs may be a value equal to between about 1% and about 25% of the order quantity, rounded up to the nearest whole number, or between about 1% and about 20% of the order quantity, rounded up to the nearest whole number, or between about 1% and about 15% of the order quantity, rounded up to the nearest whole number, or between about 1% and about 10% of the order quantity, rounded up to the nearest whole number. Printing these extra graphic designs allows for extra products to be manufactured associated with each JOB ID. These extra products can help to ensure that at least the order quantity number of products are made for each order accounting for expected discarding of products due to manufacturing defects in the product formation process.

Figure 4:
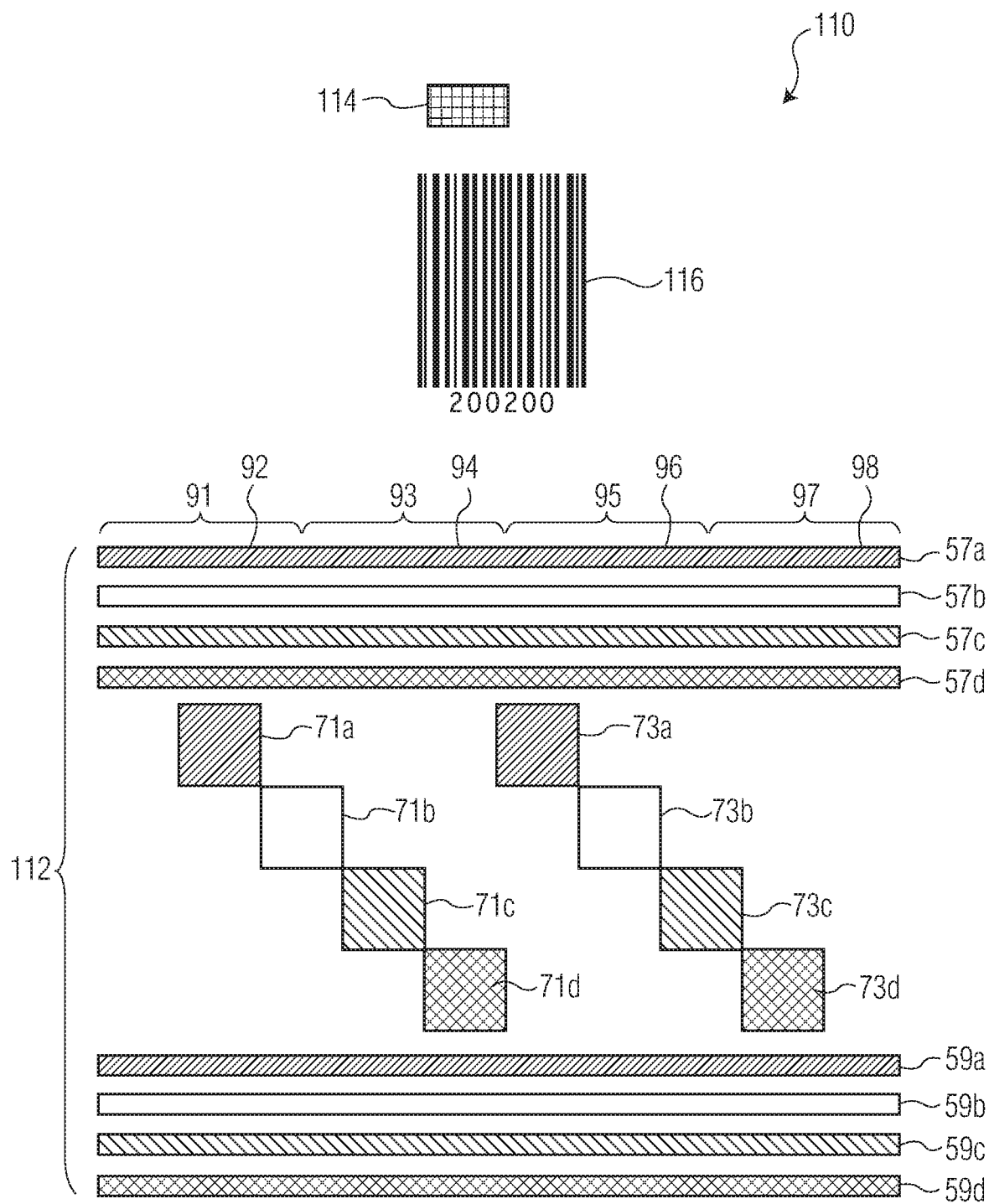
FIG. 4 is an exemplary test product graphic, according to aspects of the present disclosure.

At some point prior to the printing step detailed above, the server device 20 may be configured to generate a test product graphic for each JOB ID and associate the generated test product graphic with the corresponding JOB ID. For example, the server device 20 may generate a test product graphic for each JOB ID and store the test product graphic as one of the order components associated with the JOB ID. An exemplary test product graphic 110 is shown in FIG. 4. Each test product graphic 110 may comprise a print test graphic 112, an indicator graphic 114, and a JOB ID order identifier graphic 116.

The print test graphic 112 is a printed graphic against which a number of measurements may be made by the manufacturing apparatus 30 as part of a print quality inspection. The measurements may determine an amount of unalignment or uncoordinated phasing of either print heads within a print bar or between print bars. As can be seen in FIG. 4, the print test graphic 112 comprises print lines 57a-d and 59a-d, along with print blocks 71a-d and 73a-d. The print lines 57a-d and 59a-d and print blocks 71a-d and 73a-d are shown with different hatching (or no hatching) to represent that the print lines 57a-d and 59a-d and print blocks 71a-d and 73a-d may comprise different colors. The indicator graphic 114 may comprise a predetermined graphic located in a predetermined position on the substrate material 60 which can be detected by an inspection system. In some embodiments, the indicator graphic 114 may comprise an easily identifiable marking. For example, indicator graphic 114 may be colored to have high contrast (illustrated by the straight, crossing lines hatching) relative to the substrate on which the indicator graphic 114 is printed for easier detection. Detection of the indicator graphic 114 may trigger one or more operations in the printing apparatus 100 or the product manufacturing apparatus.

The JOB ID order identifier graphic 116 may be a graphic that correlates with the JOB ID in the manufacturing queue 23. For instance, the JOB ID order identifier graphic 116 may comprise a barcode or a matrix barcode that, when scanned by a reader, causes the reader to generate a JOB ID parameter corresponding to a customer order and/or cause the manufacturing apparatus 30 to take one or more actions.

When the printing apparatus 100 is printing each customer order, according to the JOB ID sequencing in the manufacturing queue 23, the printing apparatus 100 may be configured to print a test product graphic 110 prior the graphic designs associated with the JOB ID. This test product graphic 110 may be scanned by scanner 52 and the test product graphic 110 may be subject to a print quality test, or at least the print test graphic 112 may be subjected to a print quality inspection.

Figure 5:
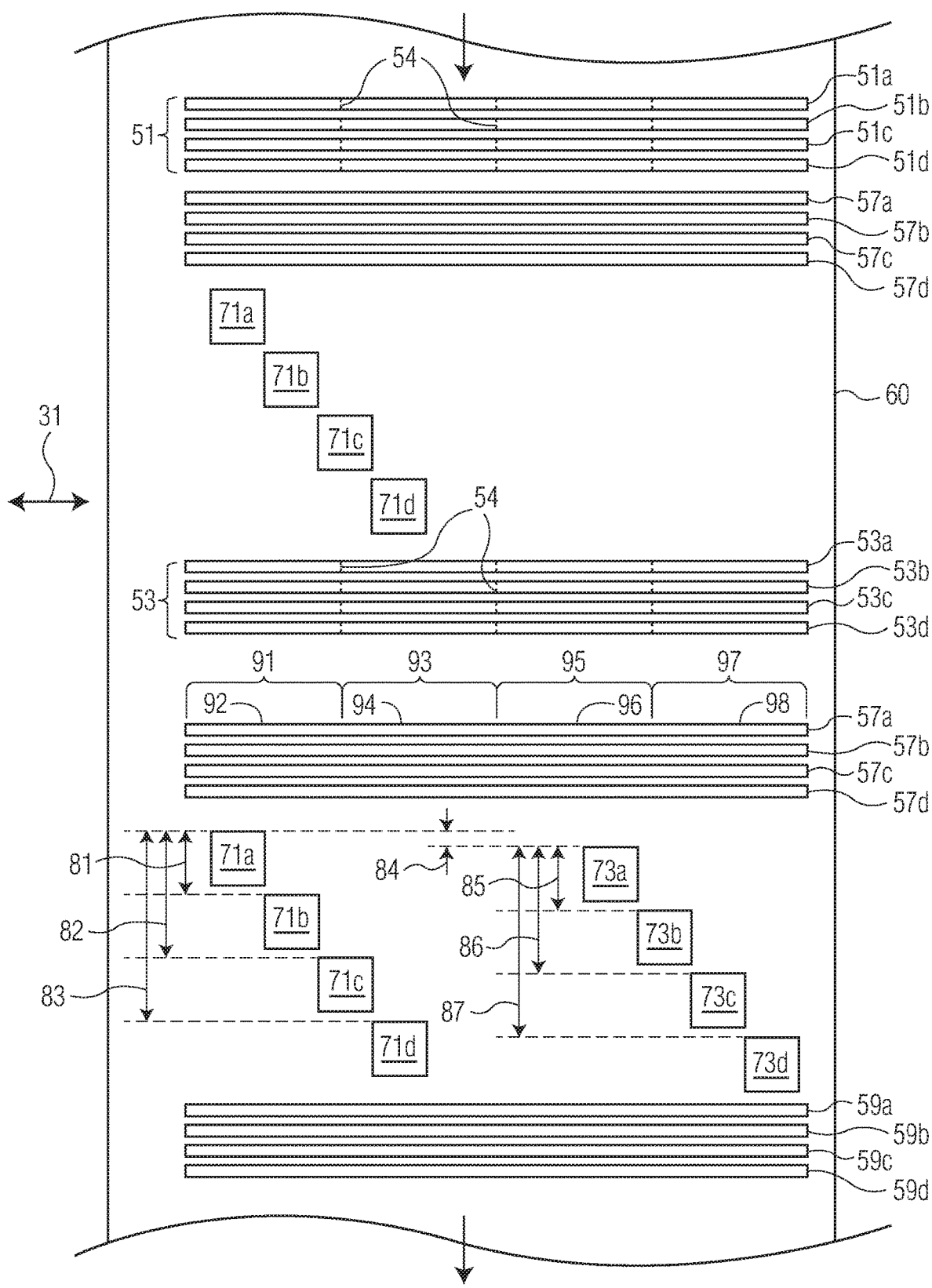
FIG. 5 is a top plan view of an exemplary printed substrate, according to aspects of the present disclosure.

The print quality inspection may generally comprise a test to ensure alignment between each print head within a single print bar, such as one of print bars 51a-d and 53a-d, for each of the print bars 51a-d and 53a-d. To achieve this test, one method, referring to FIG. 5, may be for one of the print stations 51 and 53 to print each of the print lines 57a-d of the print test graphic 112. In the embodiment of FIG. 5, the print lines 57a-d are printed by the first print station 51. Each of print lines 59a-d may be printed by the other one of the first print station 51 and the second print station 53—the second print station 53 in the machine direction of the embodiment of FIG. 5. In some embodiments, the print lines 57a-d and the print lines 59a-d may have different coloring, such as that indicated in FIG. 4.

With reference to print lines 57a-d, each of the print lines 57a-d may be broken down into line segments delineated with respect to regions 91, 93, 95, and 97, with each line segment within one of the regions 91, 93, 95, and 97 being printed by a different print head. For example, the embodiment of FIG. 5 shows each of the print bars 51a-51d and 53a-53d comprising four print heads spanning the cross-machine direction 31 of the substrate material 60. Dotted lines 54 mark the boundaries of the individual print heads in the print bars 51a-51d and 53a-53d in FIG. 5. The line segment corresponding to region 91 of print line 57a may be printed by a leftmost printhead of the print bar 51a, the line segment corresponding to region 93 of print line 57a may printed by a second leftmost printhead of the print bar 51a, and so on.

As part of the print quality inspection, each of the line segments within the regions 91, 93, 95, and 97 may be inspected to determine their relative positioning in the machine-direction (MD). For example, a trailing edge of each of the line segments within the different regions 91, 93, 95, and 97, such as line edges 92, 94, 96, and 98, may be identified for each of the line segments within the different regions 91, 93, 95, and 97. The MD offsets between each of the line edges 92, 94, 96, and 98 may be determined as a number of millimeters. For example, an MD offset between the line edges 92 and 94 may be determined, and between line edges 92 and 96, and between line edges 92 and 98. If any of the offsets are determined to be greater than about 0.1 mm, or greater than about 0.2 mm, or greater than about 0.3 mm, or greater than about 0.4 mm, or greater than about 0.5 mm, or greater than about 0.6 mm, or greater than about 0.7 mm, or greater than about 0.8 mm, the printing apparatus 100 may determine that the print test graphic 112 has failed the print quality inspection. In some further embodiments, MD offsets may further be determined between line edges 94 and 96, and between line edges 94 and 98, and between line edges 96 and 98 and compared to determine whether the print test graphic 112 has failed the print quality inspection. It should be understood that leading edges, or other features, of the line segments within the regions 91, 93, 95, and 97 could be used to determine offsets.

In at least some further embodiments, the print quality inspection may comprise a test to ensure alignment between multiple print stations, such as print stations 51 and 53. To achieve such a test, a first one of first print station 51 and the second print station 53 may print each of the print blocks 71a-d, with each of the print blocks 71a-d being printed by a different one of the print bars 51a-d or 53a-d. A second one of the first print station 51 and 53 may print each of the print blocks 73a-d, with each of the print blocks 73a-d being printed by a different one of the print bars 51a-d or 53a-d. The print blocks 71a-d and 73a-d are printed so as to align print block 71a, printed by a first one of print stations 51 and 53, with print block 73a, printed by a second of print stations 51 and 53. The print blocks 71b-d and 73b-d are printed in this manner as well. In some embodiments, the print blocks 71a-d and the print blocks 73a-d may have different coloring, such as that indicated in FIG. 4.

In embodiments where the print quality inspection tests the printing alignment between the print stations 51 and 53, the printing apparatus 100 may compare MD offsets between the print blocks 71a-d and 73a-d. For example, a reference print block may be identified, such as print block 71a. MD offsets, such as offsets 81-87, between each of the other print (blocks 71b-d and 73a-d in the present example) and the reference print block (block 71a in the present example) may be determined. Then, the offsets of corresponding print blocks are compared to determine any difference in offsets. For example, the MD offset between the reference block, 71a, and the print block 71b is offset 81. The MD offset between the reference block, 71a, and the print block 73b is offset 85. The offset 81 is compared with the offset 85 to determine any difference. If the difference is greater than about 0.1 mm, or greater than about 0.2 mm, or greater than about 0.3 mm, or greater than about 0.4 mm, or greater than about 0.5 mm, or greater than about 0.6 mm, or greater than about 0.7 mm, or greater than about 0.8 mm, the printing apparatus 100 may determine that the print test graphic 112 has failed the print quality inspection. This same analysis is done for each of the print block pairs 71b and 73b, 72c and 73c, and 71d and 73d. For print blocks 71a and 73a, an MD offset value 84 is determined and compared to a threshold, such as any of the thresholds described above. If the offset value is greater than or equal to the threshold, the printing apparatus 100 may determine that the print test graphic 112 has failed the print quality inspection.

In some embodiments, the print quality inspection may only test alignment between the print heads within each of print bar, such as print bars 51a-d and/or 53a-d, as described above. In other embodiments, the print quality inspection may only test for alignment between different print stations, such as stations 51 and 53, as described above. In still further embodiments, the print quality inspection may test alignment between the print heads within each of print bar and alignment between different print stations.

If the apparatus 100 determines that the print test graphic 112 failed the print quality inspection, the printing apparatus 100 may take one or more actions. In some embodiments, the control module 65 of the printing apparatus 100 may cause an electronic flag to be set associated with the JOB ID associated with the print test graphic 112 which failed the print quality inspection. This electronic flag may cause the products associated with the JOB ID to be culled during the product manufacturing process performed by the manufacturing apparatus 30. In other embodiments, the control module 65 may cause the test product graphic 110 to be modified in one or more ways. For example, the control module 65 may cause the printing apparatus 100 to print over the JOB ID order identifier graphic 116, such as at print station 55. In one example, the printing apparatus 100 may print over the JOB ID graphic order identifier 116 such that the manufacturing apparatus 30 is unable to reference a specific JOB ID when the JOB ID order identifier graphic 116 is read by a scanner device of the manufacturing apparatus 30. In some embodiments, the control module 65 may further instruct the server device 20 to place the JOB ID associated with the print test graphic 112 which failed the print quality inspection back into the batch queue 21 so that the customer order may be manufactured again. In other embodiments, the control module 65 may cause the printing apparatus 100 and/or server 20 to perform any combination of these actions.

Figure 6:
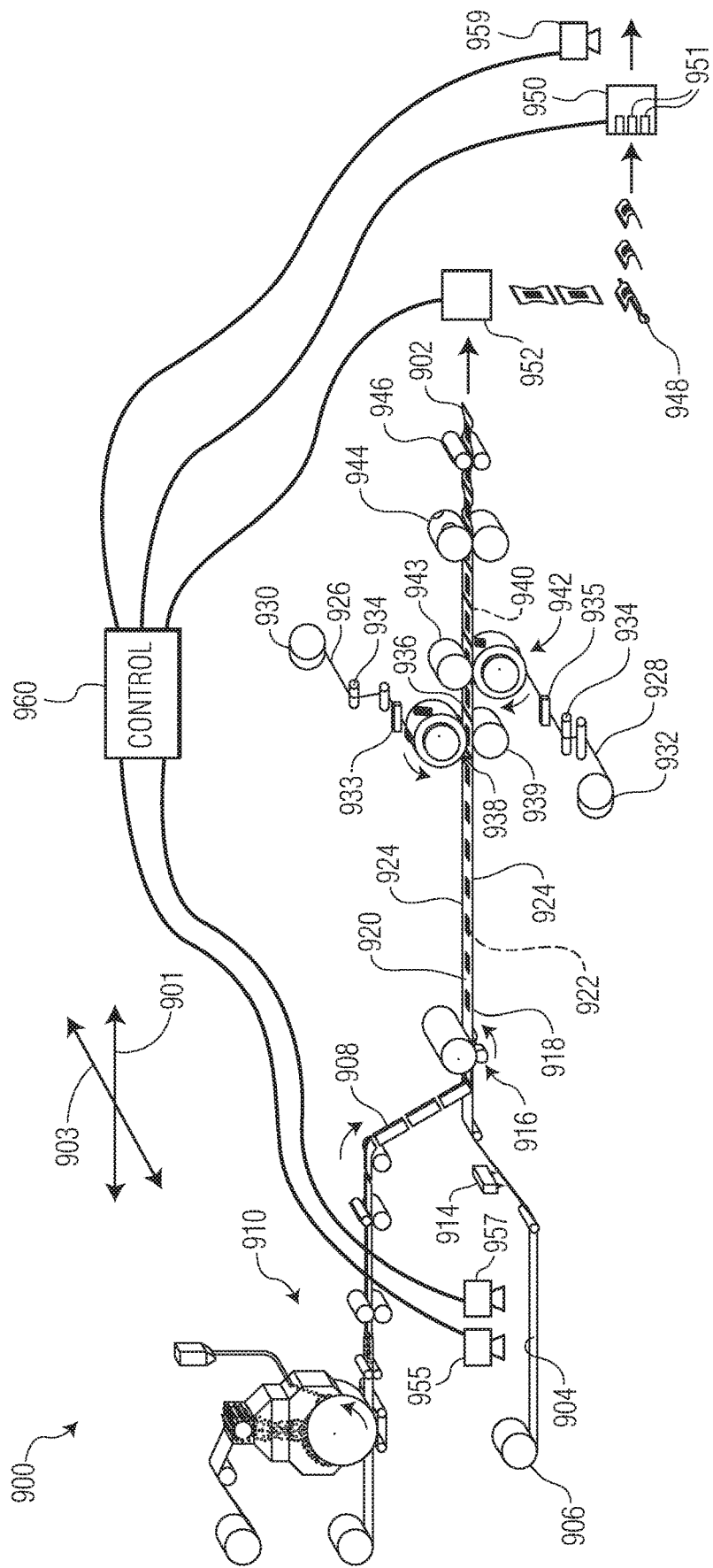
FIG. 6 is a schematic depiction of an exemplary product manufacturing apparatus according to aspects of the present disclosure.

As mentioned, in an off-line process, after the printing apparatus 100 has completed printing the graphic designs onto the substrate material 60 according to the manufacturing queue 23, the printed-substrate material 63 may form a roll. This roll of printed-substrate material 63 may be transferred to a product manufacturing apparatus 30. Product manufacturing apparatus 30 may be any suitable manufacturing apparatus which is capable of converting the printed-substrate material 63 into a series of products. One exemplary embodiment of a manufacturing apparatus 30 is depicted in FIG. 6 and labeled as product manufacturing apparatus 900. The printed-substrate material 63 may be used as an outer cover material and may be combined with one or more components in order to form a finished product, such as an absorbent article. Although the printing apparatus 100 and the product manufacturing apparatus 900 are described herein a separate apparatuses, the printing apparatus 100 may be a part of the product manufacturing apparatus 900 in some embodiments. In such embodiments, the substrate material 60 may not need to be rolled. Rather, the substrate material 60 may be printed to form printed-substrate material 63, which is then continues on in the product manufacturing apparatus 900 without being rolled.

The product manufacturing apparatus 900 of FIG. 6 may comprise continuous supply of material 904 used to form an article chassis is provided from a suitable supply source 906 in the machine direction 901. Various components of the absorbent article can be disposed on and/or bonded to the chassis material 904 as the material travels in the machine direction 901, as described below. The chassis material 904 may comprise at least a printed substrate material, such as printed substrate material 63. Alternatively, where the printing apparatus 100 is not separate from the product manufacturing apparatus 900, the chassis material 904 may comprise substrate material 60 which is printed on while being processes by the product manufacturing apparatus 900 to become a printed substrate such as substrate 63.

A plurality of absorbent assemblies 908 are provided from a suitable supply source such as, for example, an absorbent assembly forming module 910 configured to form an absorbent assembly. In the illustrated embodiment, the absorbent assemblies 908 are delivered in the machine direction 901 and disposed intermittently on the continuously moving chassis material 904, one for each absorbent article. In another suitable embodiment, a continuous web assembly including a backsheet, a bodyside liner, and an absorbent structure can be supplied by the absorbent assembly forming module 910 and subsequently cut by a cutter 946 forming the absorbent article 902.

Adhesive can be applied to the chassis material 904 from an adhesive applicator 914 located downstream of the chassis material supply source 906 for adhering the absorbent assemblies 908 to the chassis material 904. The adhesive may be applied continuously or intermittently to the chassis material 904.

In addition to or instead of adhering the absorbent assemblies 908 to the chassis material 904, the absorbent assemblies 908 and chassis material 904 can be transported through a bonding station 916 located downstream of the chassis material supply source 906 and the absorbent assembly supply source 910 to attach the absorbent assemblies 908 to the chassis material 904 and form a continuous web assembly 918 of chassis material 904 and absorbent assemblies 908. In one suitable embodiment, for example, the bonding station 916 includes a laminator roll and/or a chill roll configured to press the absorbent assemblies 908 against the chassis material 904, and adhere the absorbent assemblies 908 to the chassis material 904 with the adhesive applied to the chassis material 904 by the adhesive applicator 914. In another suitable embodiment, the bonding station 916 may include a rotary ultrasonic horn and an anvil roll configured to point bond the absorbent assemblies 908 (e.g., the bodyside liner and/or the backsheet of the absorbent assembly) to the chassis material 904 with or without the adhesive applied by the adhesive applicator 914.

The web assembly 918 has a body-facing side 920 defined by the chassis material 904 and the absorbent assembly and a garment-facing side 922 defined by the chassis material 904. The web assembly 918 also includes laterally opposing side edges 924 which, in the illustrated embodiment, are defined by laterally opposing side edges of the chassis material 904.

Two continuous webs of suitable waist elastic materials 926, 928 used to form the bodyside and garment-side waist elastic members are provided in the cross-machine direction 903 from suitable supply sources 930, 932, respectively. The supply sources 930, 932 can comprise any suitable mechanism. In the illustrated embodiment, each web of waist elastic material 926, 928 is supplied by a single supply source 930, 932, respectively. It is understood, however, that one or both of the waist elastic materials 926, 928 can be supplied by more than one supply source, such as, for example, two, three, four, five, or any other suitable number of supply sources. Each of the webs of waist elastic material 926, 928 is stretched along the direction in which the webs are fed using a plurality of tensioning rolls 934.

An adhesive applicator 933 applies adhesive to the web of waist elastic material 926 for applying the waist elastic material 926 to the body-facing side 920 of the web assembly 918. Similarly, an adhesive applicator 935 applies adhesive to the web of waist elastic material 928 for applying the waist elastic material 928 to the garment-facing side 922 of the web assembly 918. In one suitable embodiment, the adhesive applicators 933, 935 apply an elastic construction adhesive to the webs of waist elastic material 926, 928, respectively, although any suitable adhesive may be applied by the adhesive applicators 933, 935.

The web of waist elastic material 926 used to form the bodyside waist elastic members is cut to form a plurality of discrete segments 936 of waist elastic material, oriented with respect to the web assembly 918, and applied to the body-facing side 920 of the web assembly 918 at a cutting, orienting, and application station 938. The discrete segments 936 are maintained in a stretched configuration during the cutting, orienting, and application process.

In the illustrated embodiment, the discrete segments 936 are oriented generally in the cross-machine direction 903 before being applied to the web assembly 918, which is traveling in the machine direction 901. Exemplary methods and apparatus for attaching discrete segments in a cross-machine direction to a web moving in a machine direction are described in U.S. Pat. No. 6,899,780 issued May 31, 2005 to Rajala et al., which is incorporated herein by reference. In addition, before the discrete segments 936 are applied to the web assembly 918, the discrete segments 936 may be registered with the position of the web assembly 918 and/or with respect to the position of the web of waist elastic material 928 used to form garment-side waist elastic members to facilitate proper alignment of the waist elastic members on the absorbent article 902.

The discrete segments 936 of waist elastic material are bonded to the body-facing side 920 of the web assembly 918 at a bonding station 939 using any suitable bonding technique. In one suitable embodiment, the discrete segments 936 of waist elastic material 926 are point bonded to the web assembly 918 using pressure, adhesive, thermal and/or ultrasonic bonding. In another suitable embodiment, the discrete segments 936 of waist elastic material 926 are bonded to the web assembly 918 without the elastic construction adhesive applied by adhesive applicator 933.

The web of waist elastic material 928 used to form the garment-side waist elastic members is attached to the web assembly 918 using a similar process as that used to attach bodyside waist elastic members. More specifically, the web of waist elastic material 928 used to form the garment-side waist elastic members is cut into a plurality of discrete segments 940 of waist elastic material, oriented with respect to the web assembly 918, and applied to the garment-facing side 922 of the web assembly 918 at a cutting, orienting, and application station 942. The discrete segments 940 are maintained in a stretched configuration during the cutting, orienting, and application process. In the illustrated embodiment, the discrete segments 940 are oriented generally in the cross-machine direction 903 before being applied to the web assembly 918, which is traveling in the machine direction 901. In addition, before the discrete segments 940 are applied to the web assembly 918, the discrete segments 940 may be registered with the position of the web assembly 918 and/or with respect to the position of the discrete segments 936 used to form the bodyside waist elastic members to facilitate proper alignment of the waist elastic members on the absorbent article 902. In one suitable embodiment, for example, the discrete segments 940 are cut, oriented, stretched, and/or registered with the position of the web assembly 918 such that the laterally opposing side edges of the discrete segments 940 are aligned with the laterally opposing side edges 924 of the web assembly 918 when the discrete segments 940 are attached to the web assembly 918. In another suitable embodiment, both discrete segments 936, 940 are cut, oriented, stretched, and/or registered with the position of the web assembly 918 and with respect to one another such that the laterally opposing side edges of the discrete segments 936, 940 and the web assembly 918 are all aligned when the discrete segments 936, 940 are attached to the web assembly 918.

The discrete segments 940 of waist elastic material are bonded to the garment-facing side 922 of the web assembly 918 at a bonding station 943 using any suitable bonding technique. In one suitable embodiment, the discrete segments 940 of waist elastic material 928 are point bonded to the web assembly 918 using pressure, adhesive, thermal and/or ultrasonic bonding. In another suitable embodiment, the discrete segments 940 of waist elastic material 928 are bonded to the web assembly 918 without the elastic construction adhesive applied by adhesive applicator 935.

Next in the illustrated embodiment, a shaping mechanism 944 selectively removes portions of the web assembly 918 to provide a desired shape, such as curved side edges for leg openings. Such shaping mechanisms are generally known to those skilled in the art and can include, for example, rotary die cutters, oscillating water cutters, and lasers. Next, a cutter 946 selectively cuts the web assembly 918 into discrete, partially assembled absorbent articles 902. Such cutters 946 are generally known to those skilled in the art and can include, for example, the combination of a cutting roll and an anvil roll through which the web assembly 918 travels. In the illustrated embodiment, the web assembly 918 is cut along a mid-line of at least one of the discrete segments 936, 940 such that a single discrete segment 936, 940 of waist elastic material forms a waist elastic member in two different absorbent articles 902 (e.g., a leading absorbent article and a trailing absorbent article). In the illustrated embodiment, the mid-line is a bisecting line, although it is contemplated that the mid-line along which the discrete segments 936, 940 are cut can be off-set from the center of the discrete segments such that the resulting waist elastic members of a leading absorbent article 902 have a different width than the waist elastic members of a trailing absorbent article 902.

In general, the product manufacturing apparatus 900 may comprise control circuitry 960 configured to control at least scanners 955, 957, 959, inspection and culling station 952 and stacker 950. The control circuitry 960 may comprise one or more general purpose computers configured with software to receive data from, and communicate data to, the various devices 955, 957, 959, 952, and 950 and/or other devices such as server 20. In other embodiments, the control circuitry 960 may be application-specific circuitry configured to receive data from, and communicate data to, the various devices 955, 957, 959, 952, and 950 and/or other devices such as server 20. The control circuitry 960 may be configured to instruct portions of the product manufacturing apparatus 900 to take one or more actions according to such received data from the various devices 955, 957, 959, 952, and 950 and/or other devices such as server 20, as described herein.

The product manufacturing apparatus 900 may inspect the absorbent articles 902 at inspection and culling station 952. For example, the control circuitry 960 may receive image data from a scanner which is part of the inspection and culling station 952 and make a determination about each absorbent article 902 in relation to one or more quality metrics. For example, the control circuitry 960 may determine whether the absorbent articles 902 comprise one or more defects, such as missing or mis-aligned components, foreign objects, and other such defects.

The control circuitry 960 may process the image data received from the inspection and culling station 952 to form one or more parameters associated with each of the absorbent articles 902. The control circuitry 960 may further compare the one or more parameters with thresholds and/or stored parameters in order to make a determination about one or more quality metrics related to each of the inspected absorbent articles 902. For example, the control circuitry 960 may determine that an absorbent article 902 meets a foreign object quality metric if the absorbent article 902 has a number of foreign objects within the absorbent article 902 less than a threshold number of foreign objects. As another example, the control circuitry 960 may determine that an absorbent article 902 meets an alignment quality metric if a first component of the absorbent article 902 is skewed in relation a second component of the absorbent article 902 less than a skew threshold number of degrees. Of course, other quality metrics may be used, as is known in the art.

If an absorbent article 902 does not meet one or more of the quality metrics, the control circuitry 960 may cause the absorbent article 902 to be culled from the product manufacturing apparatus 900. Although shown as a single station 952, in further embodiments the inspection and culling steps may be split. For example, the inspection of the articles 902 may be performed prior to the folding station 948, and the culling step may occur after the folding station 948. Or, the inspection of the articles 902 may be performed after the folding station 948, and the culling step may occur prior to the folding station 948. In still further embodiments, the inspection and culling station 952 may be located after the folding station 948. Although, this is just one example of how the inspection and culling steps may be split in the system 900.

The absorbent articles 902 are then folded at a folding station, indicated generally at 948, using a suitable folding mechanism (e.g., blade folders, linear folders, book folders, tucker blades). In one suitable configuration, the articles 902 are folded about a fold line generally bisecting the training pant. As such, the front and back waist regions 22, 24 of each article are positioned in facing relationship. Once the articles 902 are folded they can be sent to the stacker 950 and packaged into a primary packaging.

The stacker 950 may be a conventional stacker comprising individual slots 951 for individual products, where the slots 951 continually advance around the stacker 950 to allow for consecutive products to be slotted into consecutive slots 951. As a leading product reaches a set point (such as a predetermined position) within the stacker 950, the stacker 950 (or the control circuitry 960 controlling the stacker 950) determines if there are products in consecutive slots 951 after the leading product equal to a predetermined quantity, such as a bag quantity. If there are enough products in each slot 951 after the leading product, and including the leading product, to equal the bag quantity, the stacker 950 is configured to perform a stripping action (or the control circuitry 960 is configured to cause the stacker 950 to perform a stripping action) and strip the contents of a number of slots 951 equal to the bag quantity into a primary package, such as a bag.

If there are not enough products in consecutive slots 951 after the leading product, and including the leading product, to equal the bag quantity, the stacker 950 does not perform a stripping action (or the control circuitry 960 does not cause the stacker 950 to perform a stripping action). Instead, the stacker 950 advances (or the control circuitry 960 causes the stacker 950 to advance) the slots 951 and the product in the slot 951 immediately subsequent to the slot 951 comprising the leading product becomes a new leading product. The stacker 950 (or the control circuitry 960) then performs the above described quantity check again.

In other embodiments, the stacker 950 may be configured (or the control circuitry 960 may be configured to cause the stacker 950) to advance a predetermined number of slots 951 after determining there are not enough products in consecutive slots 951 after the slot 951 comprising leading product, and including the leading product, to equal the bag quantity. In some embodiments, such a predetermined quantity may equal a bag quantity number of slots 951 in one example. In other embodiments, the predetermined quantity may be less than equal the bag quantity number of slots 951. The stacker 950 (or the control circuitry 960) may determine there are not enough products in consecutive slots 951 after the slot 951 comprising leading product, and including the leading product, to equal a bag quantity if, for example, there are empty slots 951 within a quantity of slots 951 equal to the bag quantity prior to (and including) the slot 951 comprising the leading product.

In some embodiments, the product manufacturing apparatus 900 may include an inspection system 955 capable of detecting the indicator graphic 114. For example, the inspection system 955 may be a vision system comprising a sensor (such as a camera or other detector) and a processor. The processor may be configured to receive data from the sensor and process the data and identify one or more features in the received data. When the processor finds the one or more features in the data, the processor can initiate a detection event. When initiating a detection event, the processor of the inspection system 955 may cause the manufacturing apparatus 900 to trigger scanner 957 to read the JOB ID order identifier graphic 116 associated with the indicator graphic 114. Upon successful scanning of the JOB ID order identifier graphic 116, the product manufacturing apparatus 900 may take one or more actions. A successful reading of the JOB ID order identifier graphic 116 may be scanning the JOB ID order identifier graphic 116 and correlating the JOB ID graphic 116 with an ORDER ID. In other embodiments, the inspection system 955 may comprise just a sensor and the control circuitry 960 may perform the function of the processor. Although the system 955 and the scanner 957 are shown as located prior to combining the material 904 with the absorbent assemblies, in other embodiments, the system 955 and the scanner 957 may be located after the inspection and culling station 952.

In some embodiments, after successful detection of the JOB ID order identifier graphic 116, the control circuitry 960 may cause the product manufacturing apparatus 900 to insert a predetermined number empty slots 951 into the stacker 950. For example, the control circuitry 960 may cause the product manufacturing apparatus 900 to cull such a predetermined number of products immediately preceding the product containing the test product graphic 110, such as at culling station 952 prior to the stacker 950. The predetermined number may be anywhere between one product and twenty products, or between one product and ten products, or between on product and five products, and may be two products in some embodiments. This culling step creates the predetermined number of empty slots 951 in the stacker 950, as the products are culled instead of being inserted into slots 951 in the stacker 950. In other embodiments, the control circuitry 960 may cause the stacker to advance slots 951 equal to the predetermined number. This advancement occurs prior to the slots 951 receiving products such that slots 951 remain empty within the stacker 950.

The insertion of the predetermined number of empty slots 951 in the stacker 950 ensures that the stacker 950 will skip the stripping action where the empty slots 951 are located at slot positions within the bag quantity number of slots 951 from a leading product, when the leading product is at the set point within the stacker 950. As these empty slots 951 advance in the stacker 950, the product containing the test product graphic 110 advances just behind the empty slots 951. Ultimately, the product containing the test product graphic 110 becomes a leading product with the products behind the product containing the test product graphic 110 being products with graphic designs according to the JOB ID associated with the indicator graphic 114 of the test product graphic 110.

Once the product containing the test product graphic 110 becomes the leading product, the stacker 950 will determine if there are enough products in consecutive slots 951 after and including the product containing the test product graphic 110 to equal the bag quantity. If there are enough products, the stacker 950 will strip the contents of a number of slots 951 equal to the bag quantity into a primary packaging. If there are not enough products in the consecutive slots 951 after and including the product containing the test product graphic 110 to equal the bag quantity, the system 900 may communicate with the server 20 to add the ORDER ID associated with the JOB ID of the product containing the test product graphic 110 back into the batch queue 21, or otherwise ensure that the customer order associated with the JOB ID is re-manufactured.

Due to the insertion of the predetermined number of empty slots 951 immediately preceding the product comprising the test product graphic 110 within the stacker 950, the product comprising the test product graphic 110 ends up being the first product disposed in the primary package after the stacker 950 performs the strip action which includes stripping the product containing the test product graphic 110. The product containing the test product graphic 110 may be oriented within the primary package such that the JOB ID graphic order identifier 116 is visible through the primary package. For example, the primary packaging may be clear or may have a window allowing for viewing of the product containing the test product graphic 110 through the primary packaging.

As described previously, the control circuitry 960 may be configured to cause the product manufacturing apparatus 900 to produce a greater number of products than the order quantity number associated with a JOB ID. This may be to ensure that a sufficient number of products are typically made for each JOB ID which pass inspection at the inspection and culling station 952. In some embodiments, the number of products associated with each JOB ID which pass inspection are counted. To the extent that there are a number of products associated with a JOB ID which pass inspection greater than the order quantity number associated with the JOB ID, the control circuitry 960 may cause products associated with the JOB ID to be culled to result in a number of products associated with the JOB ID equal to the order quantity number. For example, once the count reaches the order quantity number associated with the JOB ID, the control circuitry 960 may cause the remaining products associated with the JOB ID to be culled, such as by the inspection and culling station 952.

In some embodiments, a customer may order a number of products less than a bag quantity. In such embodiments, the server 20 may be configured to form the manufacturing queue 23 where multiple JOB IDs associated with an order quantity order component less than the bag quantity are disposed adjacent to each other in the manufacturing queue 23 such that adding up the values of the order quantity order components associated with such adjacent JOB IDs equals a bag quantity. In such embodiments, the system 900 may be configured such that the stacker 950 strips slots 951 containing products associated with multiple, different JOB IDs into a single primary package. In such embodiments, a product comprising a JOB ID order identifier graphic 116 associated with a first customer order may be visible through the primary package while a product comprising a JOB ID order identifier graphic 116 associated with a second, different customer order may not be visible through the primary package. All of the products comprising JOB ID order identifier graphics 116 associated with different customer orders may be removed from the primary package prior.

In such embodiments where the system 900 is configured to strip products associated with multiple, different JOB IDs into a single primary package, each JOB ID may comprise an order component marking each JOB ID as either a primary JOB ID or a sub-JOB ID. Accordingly, as the product manufacturing apparatus 900 scans a JOB ID order identifier graphic 116, the control circuitry 960 may determine whether the JOB ID order identifier graphic 116 corresponds to a primary JOB ID or a sub-JOB ID. If the JOB ID order identifier graphic 116 corresponds to a primary JOB ID, the JOB ID order identifier graphic 116 may be considered a primary order identifier graphic. Where the JOB ID order identifier graphic 116 corresponds to a sub-JOB ID, the JOB ID order identifier graphic 116 may be considered a sub-order identifier graphic.

If the control circuitry 960 determines that a scanned JOB ID order identifier graphic 116 is a primary order identifier graphic, the control circuitry 960 may cause the stacker 950 to insert a predetermined number of empty slots 951, as described previously. Where the control circuitry 960 determines that a scanned JOB ID order identifier graphic 116 is a sub-order identifier graphic, the control circuitry 960 may not cause the stacker to insert the predetermined number of empty slots. In this fashion, products associated with different JOB IDs may be manufactured and be disposed within sequential slots 951 in the stacker 950 without empty slots 951 between products associated with the different JOB IDs. Therefore, products associated with different JOB IDs may end up stripped in a single stripping action by the stacker 950 into the same primary packaging.

In other embodiments, each JOB ID may comprise an order component flag indicating if a JOB ID is a primary JOB ID. When the product manufacturing apparatus 900 scans a JOB ID order identifier graphic 116, the control circuitry 960 may determine whether the JOB ID order identifier graphic 116 corresponds to a primary JOB ID. If the JOB ID order identifier graphic 116 corresponds to a primary JOB ID, the JOB ID order identifier graphic 116 may be considered a primary order identifier graphic. If the control circuitry 960 determines that a scanned JOB ID order identifier graphic 116 is a primary order identifier graphic, the control circuitry 960 may cause the stacker 950 to insert a predetermined number of empty slots 951, as described previously. Additionally, the control circuitry 960 may be configured to not insert the predetermined number of empty slots 951 into the stacker after successfully scanning a JOB ID order identifier graphic 116 on an article 902 within a bag quantity number of articles 902 subsequent to the article 902 comprising the JOB ID order identifier graphic 116 which the control circuitry 960 determined was a primary JOB ID order identifier graphic 116. Accordingly, where multiple orders comprising order quantities less than a bag quantity are formed adjacent to each other on the product manufacturing apparatus 900, such orders will not have the predetermined number of empty slots 951 between the products of the different orders in the stacker 950. In this way, when the stacker 950 strips products into a primary package, these orders will be packaged together in the primary package.

Another scanner 959 may be disposed within the product manufacturing apparatus 900 after the products have been moved into a primary package and configured to be able to read the JOB ID graphic order identifier 116 through the primary package. If the scanner 959 is successful in reading the JOB ID graphic order identifier 116, the stacker 950 is configured to route the primary package along a first route. Additionally, the product manufacturing apparatus 900 may be configured to (or the control circuitry 960 may be configured to make the product manufacturing apparatus 900) take one or more additional actions, such as printing a shipping label corresponding to the JOB ID associated with the scanned JOB ID order identifier graphic 116 and/or printing a custom card comprising text corresponding to the JOB ID associated with the scanned JOB ID order identifier graphic 116. Such a card may be subsequently inserted into the primary package or a secondary package into which the primary package is placed.

The product comprising the test product graphic 110 may additionally be removed from the primary package, resulting in the primary package containing the products, in the quantity and with the selected and/or designed graphic designs, associated with the customer order having the JOB ID associated with the JOB ID graphic order identifier 116 of the product that was removed from the primary package. A final inspection may be performed to ensure the number of products in the primary packaging equals the order quantity number associated with the customer order corresponding to the JOB ID order identifier graphic 116 of the product that was removed from the primary package. Such a final inspection may additionally and/or alternatively determine if the selected and/or designed graphic designs of the products in the primary package correspond to the customer order corresponding to the JOB ID order identifier graphic 116 of the product that was removed from the primary package. For example, the graphic designs associated with the customer order corresponding to the JOB ID order identifier graphic 116 of the product that was removed from the primary package may be displayed on a monitor to allow for a visual comparison with the printed graphic designs on the manufactured products within the primary package. The primary package may further be inserted into a secondary package which is sealed, in some embodiments. In some further embodiments, a shipping label may be printed and applied to the secondary package.

Where the scanner 959 fails to successfully read the JOB ID graphic order identifier 116, the stacker 950 may direct the primary package along a second route. The second route may lead to a bin where the product is trashed. Alternatively, the product within the primary package may be manually inspected to determine whether the product has sufficient quality to be shipped out.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

EMBODIMENTS

Embodiment 1: A method of manufacturing products having graphic designs may comprise printing a first order identifier graphic on a substrate material, the first order identifier graphic associated with a first order for a first set of products, printing a first set of one or more graphic designs on the first substrate material, the first set of one or more graphic designs associated with the first order, combining the first substrate material with one or more product components to form the first set of products, each of the products of the first set of products being associated with the first customer order and at least one of the products of the first set of products comprising the first order identifier graphic, and packaging the first set of products in a first package wherein the first order identifier graphic is visible through the first package.

Embodiment 2: The method of embodiment 1, further comprising removing at least one of the products of the first set of products which comprises the first order identifier graphic from the first package.

Embodiment 3: The method of any of the preceding embodiments, wherein the first set of products may be packaged in the first package in a series of products comprising a first end product and a second end product, and wherein one of the products comprising the first order identifier graphic may be disposed as the first end product or the second end product prior.

Embodiment 4: The method of any of the preceding embodiments, further comprising scanning the first order identifier graphic with a scanner device while the product comprising the first order identifier graphic is disposed within the first package, and printing a first shipping label comprising a first address, the first address associated with the first order.

Embodiment 5: The method of any of the preceding embodiments, further comprising scanning the first order identifier graphic with a scanner device while the product comprising the first order identifier graphic is disposed within the first package, and printing a first card comprising text, the text associated with the first order.

Embodiment 6: The method of any of the preceding embodiments, further comprising scanning the first order identifier graphic with a scanner device, comparing a number of products of the first set of products in the first package with an order quantity number associated with the first order, and if the number of products of the first set of products is equal to or greater than the order quantity number associated with the first order, performing one or more additional actions related to the first order.

Embodiment 7: The method of any of the preceding embodiments, wherein the first set of one or more graphic designs may comprise graphic designs selected by a customer.

Embodiment 8: The method of any of the preceding embodiments, wherein forming the first set of products may comprise forming a number of products for the first set of products greater than an order quantity number associated with the first order, and wherein packaging the first set of products in the first package may comprise only packaging a number of products of the first set of products equal to the order quantity number.

Embodiment 9: The method of embodiment 8, wherein packaging a number of products of the first set of products equal to the order quantity number may comprise inspecting each of the products of the first set of products for at least one quality metric, determining whether each of the products of the first set of products meets the at least one quality metric by comparing a parameter of each of the products of the first set of products with a threshold related to the at least one quality metric, counting a number of products of the first set of products which meet the at least one quality metric, each of the products which meet the at least one quality metric being considered a good product, determining the number of good products meets the order quantity number, and culling products of the first set of products after determining the number of good products equals the order quantity number.

Embodiment 10: The method of embodiment 9, wherein culling products of the first set of products after determining the number of good products equals the order quantity number may comprise culling products of the first set of products to result in a number of products of the first set of products equal to the order quantity number.

Embodiment 11: The method of any of the preceding embodiments, further comprising printing a second order identifier graphic on the substrate material, printing a second set of one or more graphic designs on the substrate material, the second set of one or more graphic designs associated with the second order, combining the first substrate material with one or more product components to form a second set of products, each of the products of the second set of products being associated with the second customer order and at least one of the products of the second set of products comprising the second order identifier graphic, packaging the second set of products in the first package, wherein the product of the second set of products comprising the second order identifier is not visible through the first package.

Embodiment 12: A method of manufacturing and packaging products having graphic designs with a manufacturing and packaging apparatus comprising a product stacker comprising slots may comprise combining, with the manufacturing and packaging apparatus, a first substrate material having a series of graphic designs printed thereon with one or more product components to form a series of products, the series of products comprising a first set of products associated with a first customer order and one product of the first set of products comprising a first order identifier graphic, the first order identifier graphic associated with the first customer order, scanning, with the manufacturing and packaging apparatus, the first order identifier graphic with a scanner and determining if the first order identifier graphic is a primary order identifier, and after determining that the first order identifier graphic is a primary order identifier, inserting a predetermined number of empty slots into the product stacker.

Embodiment 13: The method of any of the preceding embodiments, wherein inserting the predetermined number of empty slots into the product stacker may comprise culling an amount of products of the series of products equal to the predetermined number, the culled products disposed just prior to the product comprising the first order identifier graphic in the series of products.

Embodiment 14: The method of any of the preceding embodiments, wherein inserting the predetermined number of empty slots into the product stacker may comprise advancing a number of slots of the product stacker equal to the predetermined number prior to the advanced slots receiving a product from the series of products.

Embodiment 15: The method of any of the preceding embodiments, further comprising stripping, with the product stacker, the contents of a plurality of slots into a first package once a leading product of the series of products reaches a set point on the product stacker and where each of a predetermined number of slots of the product stacker subsequent to the leading product are filled with a product.

Embodiment 16: The method of any of the preceding embodiments, further comprising scanning, with the manufacturing and packaging apparatus, the first order identifier graphic with a scanner and determining if the first order identifier graphic is a sub-order identifier, and after determining that the first order identifier graphic is a sub-order identifier, not inserting a predetermined number of empty slots into the product stacker.

Embodiment 17: The method of any of the preceding embodiments, wherein the series of products may further comprise a second set of products associated with a second customer order and one product of the second set of products may comprise a second order identifier graphic, the second order identifier graphic associated with the second customer order, and further comprising packaging the first set of products and the second set of products into a first package.

Embodiment 18: The method of any of the preceding embodiments, further comprising scanning, with the manufacturing and packaging apparatus, the second order identifier graphic with a scanner and determining if the second order identifier graphic is a sub-order identifier, and after determining that the second order identifier graphic is a sub-order identifier, not inserting a predetermined number of empty slots into the product stacker.

Embodiment 19: The method of any of the preceding embodiments, further comprising removing the product of the first set of products comprising the first order identifier graphic from the first package and removing the product of the second set of products comprising the second order identifier graphic from the first package.

Embodiment 20: The method of any of the preceding embodiments, further comprising packaging the first set of products into a first package, and removing the product of the first set of products comprising a first order identifier graphic from the first package.

What is claimed is:

1. A method of manufacturing products having graphic designs, the method comprising:
    printing a first order identifier graphic on a first substrate material, the first order identifier graphic associated with a first order for a first set of products;
    printing a first set of one or more graphic designs on the first substrate material, the first set of one or more graphic designs associated with the first order;
    combining the first substrate material with one or more product components to form the first set of products, each product of the first set of products being associated with the first customer order and less than all of the products of the first set of products comprising the first order identifier graphic;
    packaging the first set of products in a first package wherein the first order identifier graphic is visible through the first package, and
    removing at least one of the products of the first set of products which comprises the first order identifier graphic from the first package.

2. The method of claim 1, wherein the first set of products are packaged in the first package in a series of products comprising a first end product and a second end product, and wherein one of the products comprising the first order identifier graphic is disposed as the first end product or the second end product.

3. The method of claim 1, further comprising:
    scanning the first order identifier graphic with a scanner device while the product comprising the first order identifier graphic is disposed within the first package; and
    printing a first shipping label comprising a first address, the first address associated with the first order.

4. The method of claim 1, further comprising:
    scanning the first order identifier graphic with a scanner device while the product comprising the first order identifier graphic is disposed within the first package; and
    printing a first card comprising text, the text associated with the first order.

5. The method of claim 1, wherein the first set of one or more graphic designs comprise graphic designs selected by a customer.

6. The method of claim 1, wherein forming the first set of products comprises forming a number of products for the first set of products greater than an order quantity number associated with the first order, and wherein packaging the first set of products in the first package comprises only packaging a number of products of the first set of products equal to the order quantity number.

7. The method of claim 6, wherein packaging a number of products of the first set of products equal to the order quantity number comprises:
    inspecting each of the products of the first set of products for at least one quality metric;
    determining whether each of the products of the first set of products meets the at least one quality metric by comparing a parameter of each of the products of the first set of products with a threshold related to the at least one quality metric;

counting a number of products of the first set of products which meet the at least one quality metric, each of the products which meet the at least one quality metric being considered a good product;

determining the number of good products meets the order quantity number; and culling products of the first set of products after determining the number of good products equals the order quantity number.

8. The method of claim 7, wherein culling products of the first set of products after determining the number of good products equals the order quantity number comprises culling products of the first set of products to result in a number of products of the first set of products equal to the order quantity number.

9. The method of claim 1, further comprising:

printing a second order identifier graphic on the substrate material;

printing a second set of one or more graphic designs on the substrate material, the second set of one or more graphic designs associated with the second order;

combining the first substrate material with one or more product components to form a second set of products, each of the products of the second set of products being associated with the second customer order and at least one of the products of the second set of products comprising the second order identifier graphic; and packaging the second set of products in the first package, wherein the product of the second set of products comprising the second order identifier is not visible through the first package.

10. The method of claim 1, wherein only a single product of the first set of products comprises the first order identifier graphic.

11. The method of claim 1, further comprising removing each of the products of the first set of products which comprises the first order identifier graphic from the first package.

12. A method of manufacturing products having graphic designs, the method comprising:

printing a first order identifier graphic on a first substrate material, the first order identifier graphic associated with a first order for a first set of products;

printing a first set of one or more graphic designs on the first substrate material, the first set of one or more graphic designs associated with the first order;

combining the first substrate material with one or more product components to form the first set of products, each product of the first set of products being associated with the first customer order and less than all of the products of the first set of products comprising the first order identifier graphic;

packaging the first set of products in a first package wherein the first order identifier graphic is visible through the first package;

scanning the first order identifier graphic with a scanner device;

comparing a number of products of the first set of products in the first package with an order quantity number associated with the first order; and if the number of products of the first set of products is equal to or greater than the order quantity number associated with the first order, performing one or more additional actions related to the first order.

13. A method of manufacturing products having graphic designs, the method comprising:

printing a first order identifier graphic on a first substrate material, the first order identifier graphic associated with a first order for a first set of products;

printing a first set of one or more graphic designs on the first substrate material, the first set of one or more graphic designs associated with the first order;

combining the first substrate material with one or more product components to form the first set of products, each product of the first set of products being associated with the first customer order and less than all of the products of the first set of products comprising the first order identifier graphic; and packaging the first set of products in a first package wherein the first order identifier graphic is visible through the first package, wherein the first set of products are packaged in the first package in a series of products comprising a first end product and a second end product, and wherein the single product comprising the first order identifier graphic is disposed as the first end product or the second end product.

* * * * *